United States Patent [19]

Manker

[11] Patent Number: 5,800,492
[45] Date of Patent: Sep. 1, 1998

[54] ADHESIVE WARMING BAG

[75] Inventor: Charles F. Manker, Lake Forest, Ill.

[73] Assignee: Prism Enterprises, Inc., San Antonio, Tex.

[21] Appl. No.: 995,347

[22] Filed: Dec. 22, 1992

Related U.S. Application Data

[63] Continuation of Ser. No. 824,045, Jan. 23, 1992, abandoned.

[51] Int. Cl.$^6$ .................................................... A61F 7/02
[52] U.S. Cl. ................................................ 607/111; 607/112
[58] Field of Search .................................. 128/399–403, 128/382; 607/108–114; 604/385.1

[56] References Cited

U.S. PATENT DOCUMENTS

| | | | |
|---|---|---|---|
| 4,049,408 | 9/1977 | Patel | 128/403 |
| 4,382,446 | 5/1983 | Truelock et al. | 128/402 |
| 4,500,316 | 2/1985 | Damilo | 604/385.1 |
| 4,501,587 | 2/1985 | Emloe | 604/385.1 |
| 4,614,189 | 9/1986 | MacKenzie | 728/402 |
| 4,834,802 | 5/1989 | Prier | 606/203 |
| 4,938,222 | 7/1990 | Bier | 128/402 |
| 5,020,711 | 6/1991 | Kelley | 128/402 |
| 5,052,387 | 10/1991 | Natali | 128/402 |
| 5,184,613 | 2/1993 | Mintz | 128/382 |
| 5,188,103 | 2/1993 | Smith | 128/402 |

OTHER PUBLICATIONS

Warmgel, Brochure, 1991.
Photocopy of both sides of heel warmer for infants, Children's Medical Ventures, Tender Sole, Children's Medical Ventures, Incorporated, 2 pages.

*Primary Examiner*—Mark S. Graham
*Attorney, Agent, or Firm*—Leydig, Voit & Mayer, Ltd.

[57] ABSTRACT

A flexible plastic warming bag may carry a flexible strip having opposed end portions. The strip is attached to the bag at at least one end portion of the strip, in which circumstance the other end portion of the strip projects across the periphery and carries an adhesive surface. Thus the bag may be rolled into essentially tubular configuration about the limb of a patient and retained there. The strip may also be attached at both ends by an adhesive, with the points of attachment being on opposed faces of the bag. The adhesive preferentially adheres to the strip end portion, so that one of the strip end portions may be peeled away, and the bag. rolled in either direction and retained in such configuration.

11 Claims, 2 Drawing Sheets

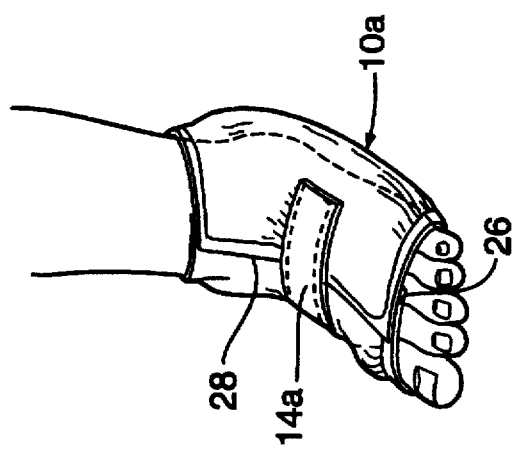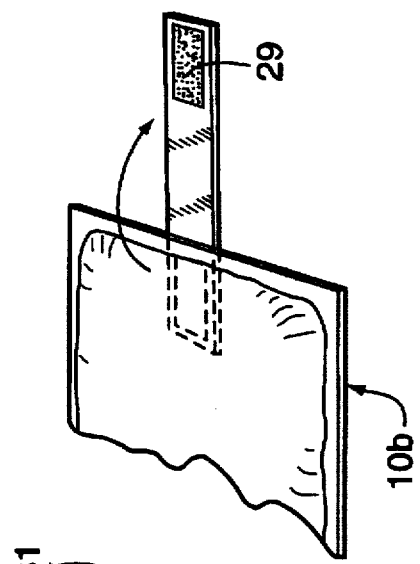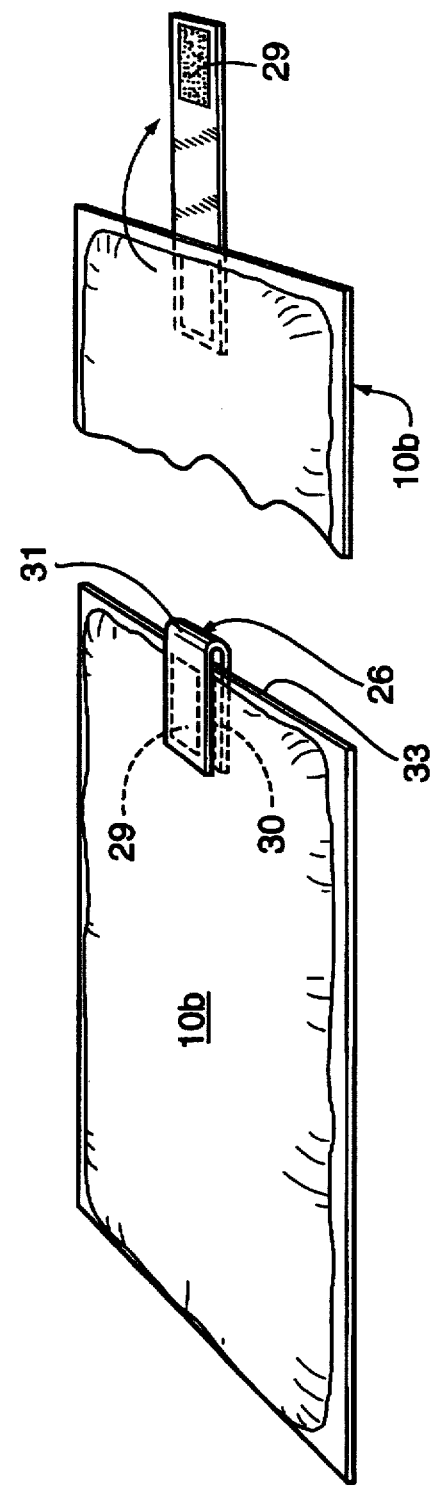

ADHESIVE WARMING BAG

This is a continuation of application Ser. No. 07/824,045 filed on Jan. 23, 1992, abandoned.

BACKGROUND OF THE INVENTION

All newborn babies are required to have a series of tests run on their blood. The preferred method of collecting a blood sample from a newborn is to use a lancet to prick the heel. After pricking, the heel typically must be squeezed to get a drop of blood to form. The squeezing frequently causes the heel to bruise and the blood sample to become contaminated. It is known that warming of the heel prior to such blood collection provides a faster flow of blood and a "cleaner" sample. This warming process takes several minutes.

Typically, a heat pack, a wash cloth, or other warming device is held to the heel of the baby for a period of time which may be as long as 15 minutes. There are several heating devices (instant heat packs) which have been designed specifically for this purpose. An example of which is the infant Heel Warmer manufactured by Prism Technologies, Inc. of Chicago, Ill. This infant heel warmer pack utilizes the heat of crystallization of sodium acetate to create warmth, and upon activation may be applied directly to the heel of the infant for the desired period of time.

A deficiency exists with the current product designs and techniques in that they must be either (1) held on the heel by the nurse for the necessary several minutes, or (2) held in place with adhesive tape which the nurse must apply. The latter application procedure is difficult to perform and requires that the nurse have a roll of tape and a "cutter" (scissors or knife) when performing the procedure.

The first method described above is obviously disadvantageous in that it takes a substantial amount of the nurses' time. The second method has the serious disadvantage of the possibility of the tape becoming inadvertently stuck to the newborn's skin and, because of the sensitivity and fragility of the skin of a newborn, resulting in considerably injury when the tape is removed. Also, it is difficult and certainly inconvenient to perform the procedure of placing the tape around the heating device (heat pack) while holding the device on the infant's foot.

Another product has been designed which involves the use of double sided tape, carried on a specially designed pack which has "flaps". This product has the disadvantage of being able to be misused by inadvertently folding the wrong "flap" inwardly first, and thus accidentally sticking the tape adhesive to the infant. In addition, the design requirements are such that the cost of such a product would be significantly increased over present products.

By my invention, a source of warmth may be applied to the heel of a patient, typically an infant, without the need for consuming substantial amounts of nursing time, and without the risk involved in using conventionally applied adhesive tape. In addition, the design can be efficiently applied to existing products without significant impact on cost. Thus a source of warmth is easily applied to the heel by this invention which may be easily removed without risk or injury.

DESCRIPTION OF THE INVENTION

By this invention, a flexible, plastic warming bag comprises a pair of opposed, flexible walls defining a sealed bag periphery and a chamber which contains a heat retentive fluid. A flexible strip having opposed end portions is attached to the bag at one of the end portions of the strip. The other end portion of the strip projects across the periphery of the bag, and carries an adhesive surface.

Accordingly, the bag may be rolled into an essentially tubular configuration and retained in such configuration by adhesion of the adhesive surface to the bag.

This is advantageous, because it permits the wrapping of the bag in its essentially tubular configuration about the heel of an infant, for example, or for any other warming use as may be desired about a limb of a patient. Also, this design reduces the risk of accidental tape adhesion to the patient's skin.

Depending on the length of the bag, the bag may either extend only partially about the limb of the patient, or it may be long enough so that its opposed ends overlap. In either case, the adhesive-carrying strip of this invention may be used to retain the two bag ends together. Thus it may be held in place about, typically, the heel of an infant.

It is often desirable for a central portion of the strip to be free of an adhesive surface. This can be accomplished by the simple use, for example, of a strip which resembles a commercial drug store bandage which has two adhesive ends, and a central portion which holds a piece of gauze. Such a structure is considered for purposes of this invention to have a central portion which is free of an adhesive surface, because the adhesive surface at the central portion is permanently covered with gauze or the like, and thus cannot function as an adhesive surface in accordance with this invention. Alternatively, plastic strips may be provided for use in this invention where only the end portions have an adhesive coating and a central portion is completely free of adhesive.

As a further alternative, substantially an entire face of the strip may carry an adhesive surface. One portion of the strip adheres to the bag, while another portion of the strip extends across the bag periphery, for adhesion to another portion of the bag after the bag has been rolled up.

Typically, exposed adhesive surfaces, such as the adhesive surface of the other end portion of the strip, are overlaid with a removable adhesive protection tab of conventional design. The tab is peeled away just prior to use, with the opposed end of the strip being brought into contact with an opposed end of the rolled bag to hold it in the desired, rolled position.

As a further embodiment, the flexible warming bag of this invention may carry a flexible strip having opposed end portions, with each end portion of the strip carrying an adhesive layer and being releasably adhered to an opposed, flexible wall of the bag by means of the adhesive layers. Such a strip may define a central portion that curves around the bag periphery so that the strip is an integral, single member. The adhesive layers at the strip end portions are designed in accordance with conventional technology to preferentially adhere to the strip end portions rather than to the bag wall, although the adhesive layers do provide adequate adhesion to the bag wall to accomplish their purpose.

Thus, either of the strip ends on the opposed bag walls may be peeled off by the user to permit the rolling of the bag into the desired, essentially tubular configuration about the limb of a patient, in either direction, with either side of the bag facing outwardly. Such a bag is very easy for a nurse to use, because she does not have to determine which way the bag must be rolled. It can be rolled either way.

Then, after rolling, the adhesive free end of the strip can be placed on the opposed end of the rolled bag to retain it in its desired, rolled configuration about the heel of an infant or the like.

DESCRIPTION OF DRAWINGS

In the drawings.

FIG. 4 is a perspective view of the bag of FIG. 3 in rolled configuration, shown to be applied to an infant's foot;

FIG. 5 is a perspective view of a third embodiment of the plastic warming bag of this invention in an original configuration; and FIG. 6 is a fragmentary perspective view of the bag of FIG. 5, shown being prepared for use.

DESCRIPTION OF SPECIFIC EMBODIMENTS

Figure 2:
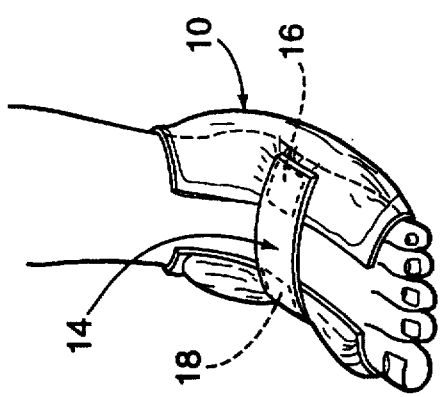
FIG. 2 is a perspective view of the plastic warming bag of FIG. 1 in rolled configuration, shown to be applied to an infant's foot.
Figure 1:
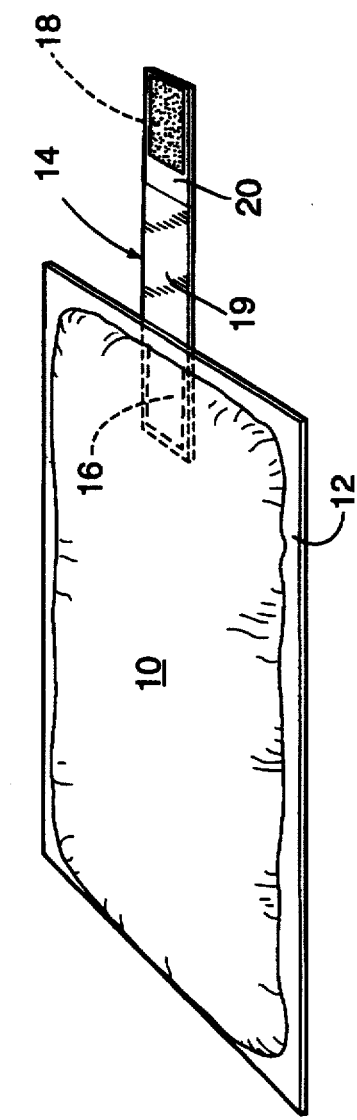
FIG. 1 is a perspective view of one embodiment of the plastic warming bag of this invention.

Referring to FIGS. 1 and 2, plastic warming bag 10 may be a polyethylene bag of conventional design, about four and three quarters inches long and three and one-half inches wide, by way of example. The embodiment of bag 10 shown defines a peripheral heat seal 12 extending around the periphery thereof. The bag may be an Infant Heel Warmer as manufactured by Prism Technologies, Inc. as described above.

In accordance with this invention, a flexible plastic strip 14 carries a pair of adhesive areas 16, 18 at opposed ends thereof. Adhesive area 16 is sealed to one wall of bag 10, while adhesive area 18 is covered with a peel away protective tab 20 of conventional design.

Thus, for use as shown in FIG. 2, protective tab 20 can be removed from the outer end of strip 14, and bag 10 can be wrapped around the foot of an infant or the like. Then, adhesive layer 18 may be applied to another portion of the bag, as shown, with strip 14 acting as a bridge to hold the two ends of bag 10 together. Central portion 19 of strip 14 is adhesive-free, so that the skin of the infant does not come into contact with adhesive.

In the particular instance shown in FIGS. 1 and 2, bag 10 is of insufficient length to completely surround the infant's heel while permitting the bag ends to overlap. If desired, a longer bag may be prepared so that the ends do overlap.

Figure 3:
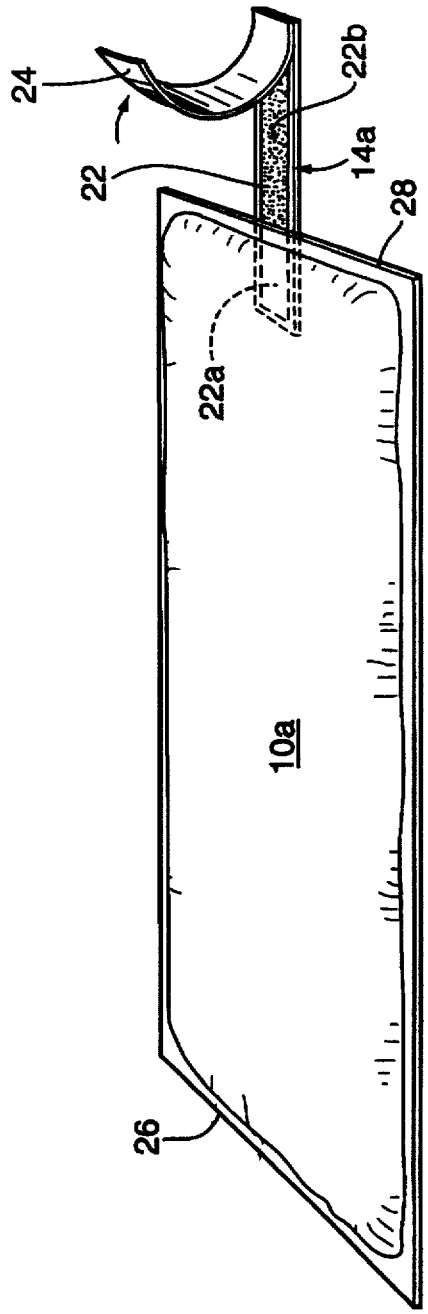
FIG. 3 is a perspective view of another embodiment of the plastic warming bag of this invention.

Such an embodiment is contemplated in the embodiment of FIGS. 3 and 4.

Referring to FIGS. 3, and 4, bag 10a may be of similar design to that of bag 10 except that it is longer, typically at least about five and one quarter inches and typically no more than ten inches long. In this embodiment, the corresponding plastic strip 14a may be similar to strip 14 of the previous embodiment except that one entire face of the strip may be coated with adhesive 22.

Thus, a portion of the adhesive layer 22a may be used to adhere strip 14a to bag 10a. The remaining portion of adhesive layer 22b may be covered with a peel release protective tab 24 until use.

Then, this bag may surround a limb of a patient such as an infant's foot as in FIG. 4, with the respective ends thereof 26, 28 overlapping each other. For this reason, there does not have to be a central, adhesive-free area similar to area 19 of strip 14 of the previous embodiment. Strip 14a thus provides complete adhesion to the bag along essentially its entire length.

Referring to FIG. 5, in this embodiment bag 10b is provided, being basically similar to the previous bag embodiments. However, in this embodiment, a plastic strip 26 is provided having respective adhesive ends 29, 30 which adhere to opposite sides of bag 10b in a releasable manner, with an adhesive-free central portion 31 of strip 26 being curved in a fold about the bag periphery 33. The particular adhesive used may be formulated or applied in a conventional manner to be more strongly bonded to the particular material of strip 26 than to the material of bag 10b, which may typically be polyethylene. Accordingly, the user may peel either one of adhesive areas 29, 30 off of the bag as shown in FIG. 6, where the peeled area is adhesive area 28. Then, bag 10b may be rolled as in the previous embodiments, and adhesive area 29 reattached to hold bag 10b in its rolled condition.

As previously stated, an advantage of this is that the bag 10b may be rolled and applied in either direction of rolling. This facilitates the job for the nurse, as described above. Also, no protective peel tabs are needed in this instance as part of the product.

The above has been offered for illustrative purposes only and is not intended to limit the scope of the invention of this application, which is as defined in the claims below.

That which is claimed:

1. A warming device comprising (a) first and second opposed flexible plastic walls sealed together to form an edge and a fluid-tight chamber, (b) a fluid disposed in said chamber which is a source of heat, (c) a flexible strip having two sides and two ends, and (d) an adhesive on said two ends of one side of said flexible strip and not on the other side of said flexible strip, said flexible strip being releasably secured to said first and second opposed plastic walls such that the side of one of said flexible strip ends containing adhesive contacts said first opposed plastic wall and the side of the other of said flexible strip ends containing adhesive contacts said second opposed plastic wall such that said flexible strip projects over said edge of said warming device and such that said flexible strip may be unsecured from either said first or second plastic wall and secured to the opposite plastic wall upon placing said warming device into an essentially tubular configuration so as to retain said warming device in such an essentially tubular configuration.

2. The warming device of claim 1, wherein said flexible strip has a central portion free of adhesive between said two ends on said side containing adhesive.

3. The warming device of claim 1, wherein said first and second plastic walls are rectangular in shape having two parallel long edges and two parallel short edges.

4. The warming device of claim 3, wherein said flexible strip is secured to said first and second plastic walls such that said flexible strip projects over one of said short edges.

5. The warming device of claim 4, wherein said flexible strip has a central portion free of adhesive between said two ends on said side containing adhesive.

6. The warming device of claim 4, wherein said warming device is of such a size to permit the wrapping of said warming device substantially around the foot of an infant.

7. The warming device of claim 6, wherein said flexible strip has a central portion free of adhesive between said two ends on said side containing adhesive.

8. The warming device of claim 4, wherein said warming device is of such a size to permit the wrapping of said warming device completely around the foot of an infant.

9. The warming device of claim 8, wherein said flexible strip has a central portion free of adhesive between said two ends on said side containing adhesive.

10. The warming device of claim 1, wherein said fluid is a supercooled salt solution which releases heat upon crystallization.

11. A warming device comprising (a) first and second opposed flexible plastic walls sealed together to form a rectangular edge and a fluid-tight chamber having two parallel long sides and two parallel short sides, (b) a supercooled salt solution disposed in said chamber which provides heat upon crystallization, (c) a flexible strip of a length less than the length of said long side of said warming device and having two sides and two ends, and (d) an adhesive on said two ends of one side of said flexible strip and not on the other side of said flexible strip nor on a central portion between said two ends of said side containing adhesive, said flexible strip being releasably secured to said first and second opposed plastic walls such that the side of one of said flexible strip ends containing adhesive contacts said first opposed plastic wall and the side of the other of said flexible strip ends containing adhesive contacts said second opposed plastic wall such that said flexible strip projects over said edge of one of said two parallel short sides of said warming device and such that said flexible strip may be unsecured from either said first or second plastic wall and secured to the opposite plastic wall upon placing said warming device into an essentially tubular configuration so as to retain said warming device in such an essentially tubular configuration.

* * * * *